(12) United States Patent
Nakamura

(10) Patent No.: US 9,733,297 B2
(45) Date of Patent: Aug. 15, 2017

(54) ELECTRIC FIELD CONCENTRATION LOCATION OBSERVATION DEVICE AND ELECTRIC FIELD CONCENTRATION LOCATION OBSERVATION METHOD

(71) Applicant: HAMAMATSU PHOTONICS K.K., Hamamatsu-shi, Shizuoka (JP)

(72) Inventor: Tomonori Nakamura, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 22 days.

(21) Appl. No.: 14/767,723

(22) PCT Filed: Feb. 13, 2014

(86) PCT No.: PCT/JP2014/053340
§ 371 (c)(1),
(2) Date: Aug. 13, 2015

(87) PCT Pub. No.: WO2014/129377
PCT Pub. Date: Aug. 28, 2014

(65) Prior Publication Data
US 2015/0377953 A1    Dec. 31, 2015

(30) Foreign Application Priority Data

Feb. 19, 2013   (JP) ................................. 2013-030022

(51) Int. Cl.
*G01R 31/26*       (2014.01)
*G01R 31/265*      (2006.01)
(Continued)

(52) U.S. Cl.
CPC ......... *G01R 31/2607* (2013.01); *G01N 21/17* (2013.01); *G01R 31/2656* (2013.01); *G01N 2021/1765* (2013.01); *G01R 31/311* (2013.01)

(58) Field of Classification Search
CPC combination set(s) only.
See application file for complete search history.

(56) References Cited

U.S. PATENT DOCUMENTS

| 5,422,498 A | 6/1995 | Nikawa et al. |
| 6,316,950 B1 | 11/2001 | Denk et al. |
(Continued)

FOREIGN PATENT DOCUMENTS

| JP | H05-136240 A | 6/1993 |
| JP | H11-340293 A | 12/1999 |
(Continued)

*Primary Examiner* — Clayton E Laballe
*Assistant Examiner* — Jas Sanghera
(74) *Attorney, Agent, or Firm* — Drinker Biddle & Reath LLP

(57) ABSTRACT

An observation apparatus includes a laser light source, a scanning optical system irradiating a semiconductor device with laser light output from the laser light source, a bias power supply applying a reverse bias voltage of a predetermined voltage between electrodes of the semiconductor device, a sensor detecting an electrical property occurring in the semiconductor device in response to the laser light, and a control system generating an electrical property image of the semiconductor device based on a detection signal from the sensor. The bias power supply gradually increases a magnitude of the predetermined voltage until the predetermined voltage reaches a voltage at which avalanche amplification occurs in the semiconductor device. When the predetermined voltage is increased, the scanning optical system irradiates with the laser light, the sensor detects the electrical property, and the control system generates the electrical property image.

11 Claims, 7 Drawing Sheets

(51) Int. Cl.
*G01N 21/17* (2006.01)
*G01R 31/311* (2006.01)

(56) References Cited

U.S. PATENT DOCUMENTS

| | | | |
|---|---|---|---|
| 6,346,821 B1 * | 2/2002 | Baumgart | G01R 31/2656 |
| | | | 257/E21.531 |
| 2012/0056626 A1 * | 3/2012 | Vedagarbha | G01R 31/311 |
| | | | 324/501 |

FOREIGN PATENT DOCUMENTS

| | | |
|---|---|---|
| JP | 2006-234789 A | 9/2006 |
| JP | 2010-181288 A | 8/2010 |
| JP | 2012-058247 A | 3/2012 |

* cited by examiner

ELECTRIC FIELD CONCENTRATION LOCATION OBSERVATION DEVICE AND ELECTRIC FIELD CONCENTRATION LOCATION OBSERVATION METHOD

TECHNICAL FIELD

The present invention relates to an electric field concentration position observation apparatus and an electric field concentration position observation method.

BACKGROUND ART

An invention relating to a method for observing a high-density semiconductor device using an optical beam induced current (OBIC) is disclosed in Patent Document 1. In the method described in this Document, a back surface of a silicon semiconductor device is irradiated with YAG laser light with a wavelength of 1064 nm or HeNe laser light with a wavelength of 1152 nm, and the OBIC current is measured.

CITATION LIST

Patent Literature

Patent Document 1: Japanese Patent Application Laid-Open No. H5-136240

SUMMARY OF INVENTION

Technical Problem

For example, in a semiconductor device such as a transistor, if there is a part on which an electric field is concentrated, damage may occur. As one example, if an electric field is concentrated on a certain part in a semiconductor device such as a power transistor for which high withstand voltage performance is required, an avalanche breakdown phenomenon occurs, a large current intensively flows to the relevant part, and there is a possibility of the device being damaged. Accordingly, when a semiconductor device is designed and fabricated, it is preferable to eliminate parts on which an electric field is concentrated as much as possible in order to increase withstand voltage performance.

In order to find whether or not there is an electric field concentration part in a semiconductor device, in general, an electric field intensity distribution is estimated by calculation and simulation. However, in this method, it is difficult to accurately find a part on which an electric field is concentrated. Further, there is no method for measuring the electric field intensity distribution in a semiconductor device that operates normally, and even if a semiconductor device in which concentration of an electric field actually occurs is examined, an electric field concentration part and its surroundings are severely damaged, and it is substantially difficult to identify the part in many cases.

The present invention has been made in view of the above problem, and an object thereof is to provide an electric field concentration position observation apparatus and an electric field concentration position observation method through which an electric field concentration part can be accurately found.

Solution to Problem

In order to solve the above problem, an electric field concentration position observation apparatus according to the present invention is an apparatus for observing an electric field concentration position in a semiconductor device, and includes: a laser light source; an irradiation optical system irradiating the semiconductor device with laser light output from the laser light source; a voltage application unit applying a predetermined voltage between electrodes of the semiconductor device; a detection unit detecting an electrical property occurring in the semiconductor device in response to the laser light; and an image generation unit generating an electrical property image of the semiconductor device based on a detection signal from the detection unit, and in the apparatus, the voltage application unit gradually increases a magnitude of the predetermined voltage until the predetermined voltage reaches a voltage at which avalanche amplification occurs in the semiconductor device, and when the predetermined voltage is increased, the irradiation optical system irradiates with the laser light, the detection unit detects the electrical property, and the image generation unit generates the electrical property image.

Further, an electric field concentration position observation method according to the present invention is a method for observing an electric field concentration position in a semiconductor device, and includes: a voltage applying step of applying a predetermined voltage between electrodes of the semiconductor device; an irradiating and detecting step of irradiating the semiconductor device with laser light and detecting an electrical property occurring in the semiconductor device in response to the laser light; and an image generating step of generating an electrical property image of the semiconductor device based on a detection signal obtained in the irradiating and detecting step, and in the method, the voltage applying step, the irradiating and detecting step, and the image generating step are repetitively performed while gradually increasing the predetermined voltage in the voltage applying step until the predetermined voltage reaches a voltage at which avalanche amplification occurs in the semiconductor device.

In the electric field concentration position observation apparatus and the electric field concentration position observation method described above, an electric field concentration part is observed by visualizing the electrical property (e.g., a magnitude of an optical beam induced current) occurring in the semiconductor device due to the laser light. Then, during the observation, a magnitude of the voltage applied between the electrodes of the semiconductor device is gradually increased until the voltage reaches a voltage at which the avalanche amplification action occurs.

When the applied voltage is low, the avalanche amplification does not occur, and thus the above-described electrical property is slightly changed, and the electric field concentration part cannot be identified. However, if the applied voltage is increased to such an extent that the avalanche amplification occurs, the above-described electrical property is greatly changed by the avalanche amplification when the electric field concentration part is irradiated with the laser light, and thus the electric field concentration position can be identified. Further, if the avalanche amplification becomes excessive, an avalanche breakdown phenomenon occurs and the semiconductor device is damaged, however, in the above-described observation apparatus and the observation method, the voltage is applied to the semiconductor device to the approximately same extent that the avalanche amplification occurs, and thus damage to the semiconductor device can be suppressed. Thus, according to the above-described observation apparatus and the observation method, the semiconductor device can be preferably observed, and the electric field concentration position can be accurately found.

Advantageous Effects of Invention

In accordance with the electric field concentration position observation apparatus and the electric field concentration position observation method according to the present invention, the electric field concentration part can be accurately found.

DESCRIPTION OF EMBODIMENTS

Hereinafter, embodiments of an electric field concentration position observation apparatus and an electric field concentration position observation method according to the present invention will be described in detail with reference to the accompanying drawings. In addition, in the description of the drawings, the same elements will be denoted by the same reference symbols, and overlapping descriptions thereof will be omitted.

(First Embodiment)

Figure 1:
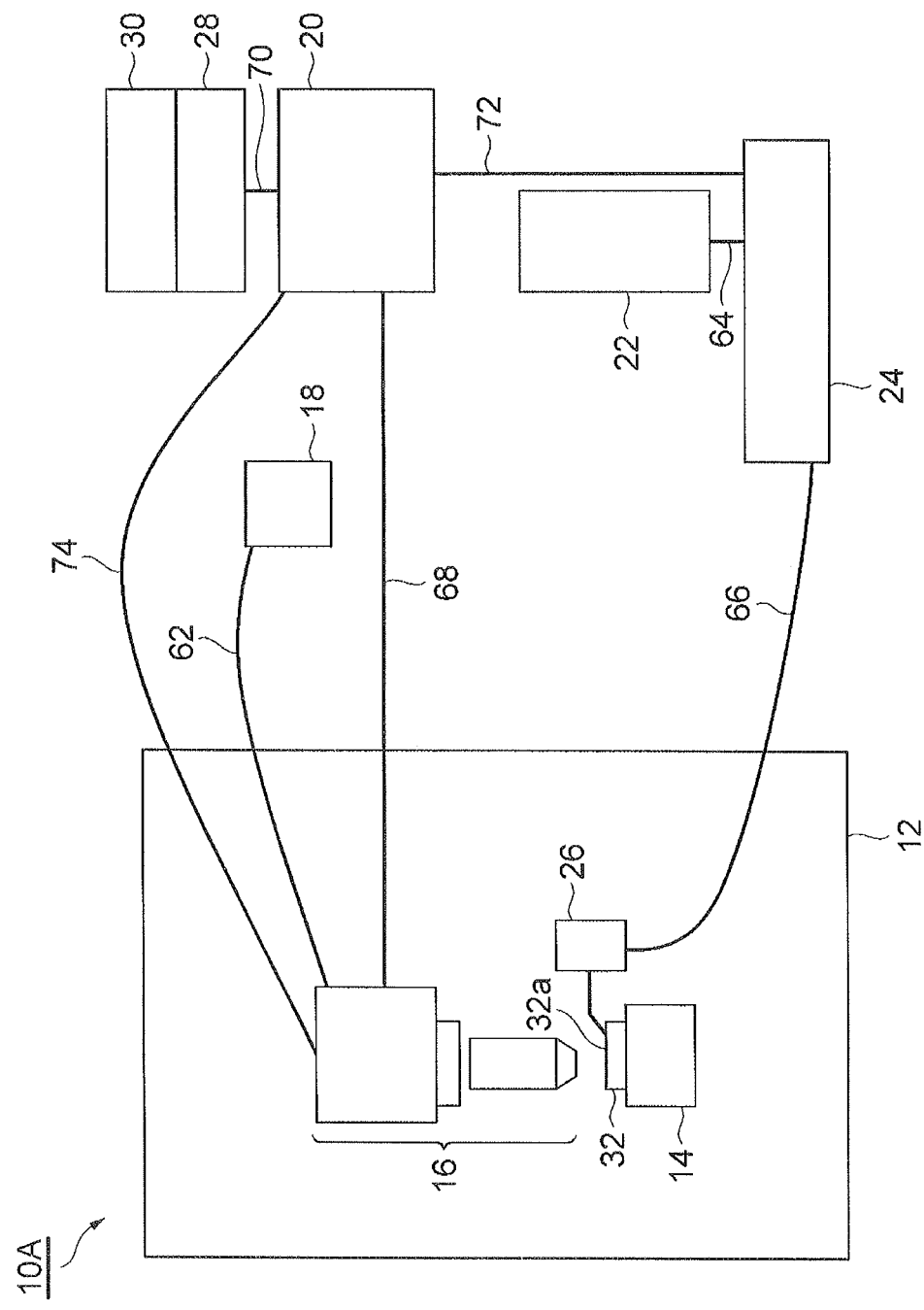
FIG. 1 is a block diagram schematically illustrating a configuration of an electric field concentration position observation apparatus according to a first embodiment.

FIG. 1 is a block diagram schematically illustrating a configuration of an electric field concentration position observation apparatus (hereinafter referred to as observation apparatus) 10A according to a first embodiment of the present invention. This observation apparatus 10A is an apparatus for identifying and observing a position on which an electric field is concentrated, for example, in a semiconductor device 32 such as a power transistor for which a high withstand voltage characteristic is required. As illustrated in FIG. 1, the observation apparatus 10A of the present embodiment includes a dark box 12, a stage 14, a scanning optical system 16, a laser light source 18, and a laser scan controller 20.

The dark box 12 is a container for shielding light from the outside, and the semiconductor device 32 that is an observation object (sample) is housed in the dark box. The stage 14 is disposed in the dark box 12, and supports the semiconductor device 32. The semiconductor device 32 is placed on the stage 14 such that a back surface thereof faces the scanning optical system 16.

The laser light source 18 outputs laser light with a suitable wavelength to produce an optical beam induced current (OBIC) in the semiconductor device 32 due to single-photon absorption. The scanning optical system 16 is an irradiation optical system in the present embodiment, and irradiates the back surface of the semiconductor device 32 with the laser light output from the laser light source 18. The laser light is collimated by the scanning optical system 16, and then is focused in the semiconductor device 32. The laser light source 18 and the scanning optical system 16 are optically coupled via an input optical fiber 62.

A suitable wavelength of the laser light varies according to band gap energy of an observation object portion in the semiconductor device 32. To be specific, photon energy of the laser light is preferably slightly greater than the band gap energy of the observation object portion. As one example, when the observation object portion is formed of Si, the band gap energy thereof is 1.12 eV (1.1 µm calculated in terms of wavelength), and, in this case, a suitable wavelength range of the laser light is 0.9 µm or more and 1.1 µm or less.

The laser light source 18 may be a so-called femtosecond laser light source that outputs pulsed laser light whose pulse width is shorter than 1 picosecond. Further, the laser light source 18 may be a so-called CW (Continuous Wave) laser light source that continuously outputs laser light.

The laser scan controller 20 controls an irradiation position of the laser light by the scanning optical system 16. The laser scan controller 20 is electrically coupled to the scanning optical system 16 via a scanner control cable 68, and is also optically coupled to the scanning optical system 16 via a return optical fiber 74.

Figure 2:
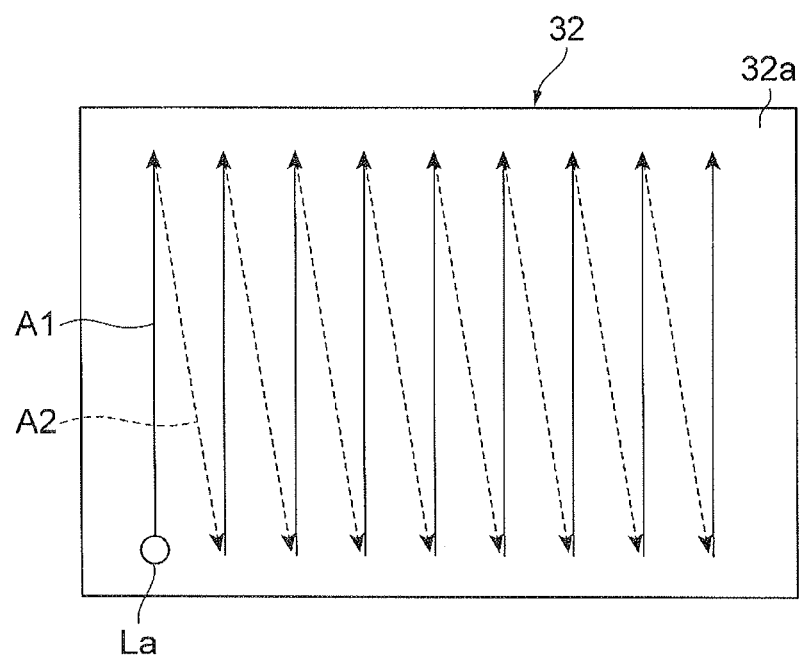
FIG. 2 is a conceptual view illustrating a state in which a scanning optical system irradiates a semiconductor device with laser light.

Here, FIG. 2 is a conceptual view illustrating a state in which the scanning optical system 16 irradiates the semiconductor device 32 with laser light La. In FIG. 2, a laser irradiation surface 32a of the semiconductor device 32 viewed in an irradiation direction of the laser light La is illustrated, and moving paths of the laser light La on the laser irradiation surface 32a are presented as arrows A1 and A2. As illustrated in FIG. 2, as the laser scan controller 20 controls the scanning optical system 16, the controller moves an irradiation point of the laser light La from one end side to the other end side of the laser irradiation surface 32a in a given direction (arrow A1), and then returns the irradiation point to the one end side of the laser irradiation surface 32a again (arrow A2), and moves the irradiation point in the above-described direction again (arrow A1). The laser scan controller 20 causes the scanning optical system 16 to repeat this operation, thereby performing scanning of the laser light La for the laser irradiation surface 32a. Here, the moving paths of the laser light La on the laser irradiation surface 32a are not limited to the unidirectional scanning as in FIG. 2, and various moving paths such as bidirectional scanning in which the direction in which the irradiation point moves is alternately changed may be adopted.

Referring to FIG. 1 again, the observation apparatus 10A of the present embodiment further includes a bias power supply 22, a sensor 24, a probing system 26, and a control system 28. The bias power supply 22 and the probing system 26 constitute a voltage application unit in the present embodiment, and apply a predetermined reverse bias voltage between electrode terminals of the semiconductor device 32. At this time, the bias power supply 22 and the probing system 26 are controlled such that a fixed voltage value (constant voltage) is applied to the semiconductor device 32.

The bias power supply 22 is a power supply generating a reverse bias voltage, and is electrically coupled to the probing system 26 via a power cable 64 and a cable 66. The probing system 26 brings a probe into contact with the electrode terminal of the semiconductor device 32, thereby applying the reverse bias voltage (predetermined voltage) to the electrode terminals of the semiconductor device 32. For example, when the semiconductor device 32 is a transistor, the probing system 26 applies the reverse bias voltage between two electrode terminals of an emitter, a collector, and a base. A magnitude of the reverse bias voltage is a magnitude at which the semiconductor device 32 generates no avalanche breakdown phenomenon.

The sensor 24 is a detection unit in the present embodiment, and detects electrical properties occurring in the semiconductor device 32 in response to the laser light. Such electrical properties may include, for example, an OBIC value associated with an OBIC phenomenon, a current change amount associated with an OBIC, and magnetic flux density (or change therein) or magnetic field intensity (or change therein) caused by the current change associated with the OBIC. Here, the sensor 24 may be configured to be able to detect a voltage value or a change in voltage value associated with the OBIC. The sensor 24 is electrically coupled to the probing system 26 via the cable 66, and detects the above-described electrical property through the cable 66.

The control system 28 is electrically coupled to the laser scan controller 20 via a control signal cable 70, and is further electrically coupled to the sensor 24 via a control signal cable 72. The control system 28 controls operations of the laser scan controller 20 and the sensor 24 in an integrated way. Further, the control system 28 controls the magnitude of the reverse bias voltage applied to the semiconductor device 32 from the probing system 26. In addition, the control system 28 is an image generation unit in the present embodiment, and generates electrical property images of the semiconductor device 32 based on detection signals from the sensor 24. The generated electrical property image is sent to and displayed on a monitor device 30.

Figure 3:
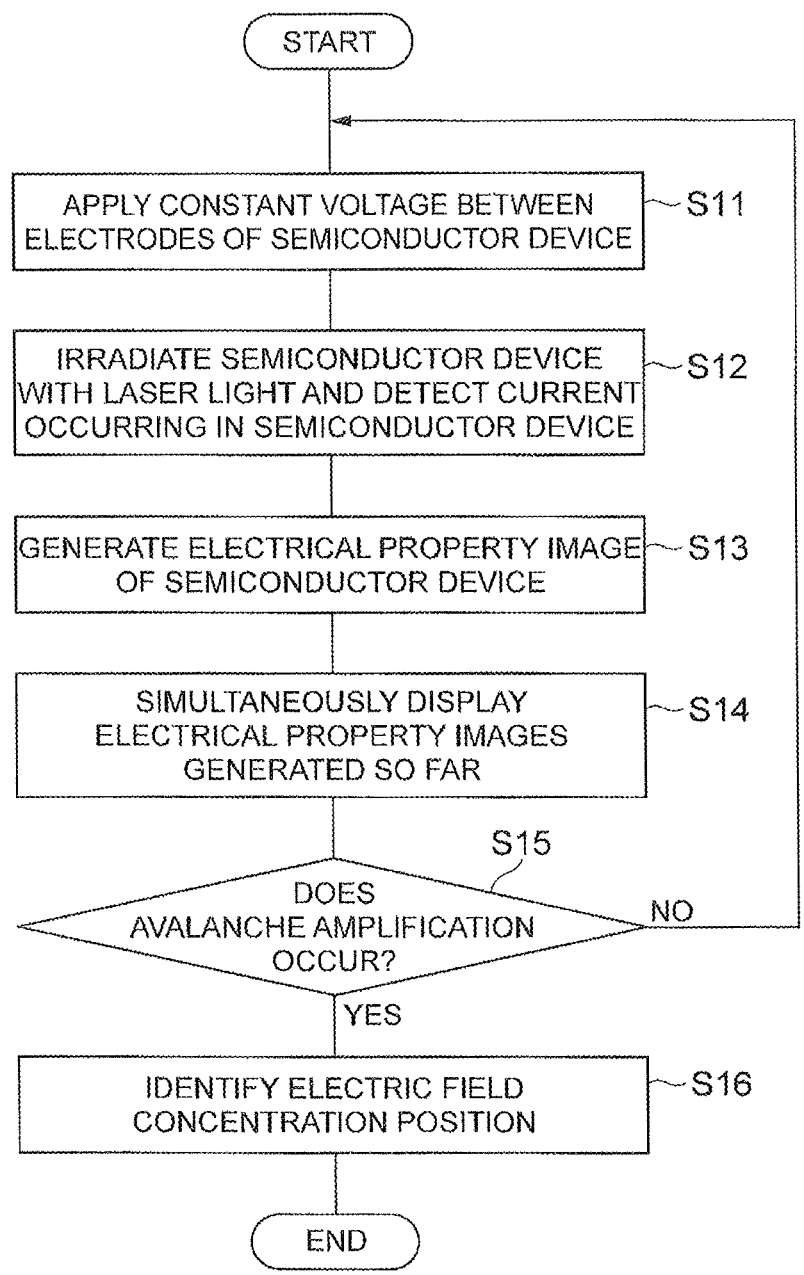
FIG. 3 is a flow chart illustrating an operation of the observation apparatus and an electric field concentration position observation method.

An operation of the observation apparatus 10A having the above configuration will be described along with an electric field concentration position observation method (hereinafter referred to as observation method) according to the present embodiment. FIG. 3 is a flow chart illustrating the operation of the observation apparatus 10A and the electric field concentration position observation method.

As illustrated in FIG. 3, first, a reverse bias voltage is applied between the electrode terminals of the semiconductor device 32 using the bias power supply 22 and the probing system 26 (voltage applying step, step S11 in FIG. 3). A magnitude of the reverse bias voltage applied first is sufficiently smaller than a minimum value (hereinafter referred to as maximum allowable voltage value) of a voltage at which an avalanche breakdown phenomenon occurs. For example, the reverse bias voltage applied first may be previously set to 0 V. Otherwise, an instruction regarding the magnitude of the reverse bias voltage may be carried out by the control system 28, or may be input by a person who operates the observation apparatus 10A. Otherwise, a value obtained by inputting the maximum allowable voltage value, and subtracting a predetermined value stored in advance in the observation apparatus 10A from the maximum allowable voltage value may be used as a first magnitude of the reverse bias voltage.

Next, in the state in which the above-described reverse bias voltage is applied, the semiconductor device 32 is irradiated with laser light using the laser light source 18 and the scanning optical system 16 (irradiating and detecting step, step S12 in FIG. 3). In the present embodiment, as illustrated in FIG. 2, the laser light La is scanned over the laser irradiation surface 32a of the semiconductor device 32. At this time, photon absorption occurs in an internal region of the semiconductor device 32 around a focal position of the laser light, and carrier pairs made up of electrons and holes are created.

Here, in the present embodiment, a wavelength causing single-photon absorption is selected as a wavelength of the laser light, however, when the laser light is femtosecond laser light, a spatial resolution is expected to be improved by a non-linear effect associated with multiphoton absorption, and a resolution in an optical axis direction can be increased in a subsequent image generating step S13. The carrier pairs created in this way disappear in a portion at which no electric field, i.e., no depletion layer, is present due to recombination, but they are guided to the electrode terminals in a portion to which the electric field is applied, and is output as the OBIC.

At this time, if the electric field in a semiconductor is locally increased and thus there is a portion at which avalanche amplification occurs, the OBIC is multiplied several times to several tens of times, and becomes a greater current. For this reason, at the moment at which the laser light La passes through such a portion, the electrical property values (as described above, for example, the current value or the current change amount of the OBIC, the magnetic flux density (or change therein) or the magnetic field intensity (or change therein) caused by the current change caused by the OBIC, the voltage value and the voltage change, etc.) are sharply increased.

If no avalanche amplification occurs at any portions, no such great change in the electrical property values occurs throughout a scanning course. In the irradiating and detecting step S12, the electrical property value occurring in the semiconductor device 32 due to the laser light is detected using the sensor 24, and a detection signal presenting the detection result is sent to the control system 28.

The control system 28 performs mapping based on the detection signals obtained in the irradiating and detecting step S12 and information on scanning positions when such detection signals are obtained, thereby generating an electrical property image of the semiconductor device 32 (image generating step, step S13 in FIG. 3). In the image generating step S13, a distribution image of data values according to the above-described electrical property values is generated, for example, within a region assumed to be the semiconductor device 32. Levels of the data values are represented, for example, by contrast of pixels.

Subsequently, the electrical property image generated in the image generating step S13 is displayed on the monitor device 30 (displaying step, step S14 in FIG. 3). Afterward, while the electrical property image displayed on the monitor device 30 is observed, while it is checked whether or not the avalanche amplification occurs, and while the reverse bias voltage is gradually increased in the voltage applying step S11 until the voltage at which the avalanche amplification occurs in the semiconductor device 32 is reached, the above-described steps, i.e., the voltage applying step S11, the irradiating and detecting step S12, the image generating step S13, and the displaying step S14, are repeatedly performed (determining step, step S15 in FIG. 3). In other words, whenever the reverse bias voltage is increased, the scanning optical system 16 irradiates with the laser light, the sensor 24 detects the electrical property value, the control system 28 generates the electrical property image, and the monitor device 30 displays the electrical property image.

Without being limited to performing the irradiating and detecting step S12 whenever the reverse bias voltage is increased, the irradiating and detecting step S12 may be performed after the reverse bias voltage is gradually increased a plurality of times. Further, the irradiating and detecting step S12 may always be performed, and when the voltage applying step S11 is performed, the image generating step S13 and the displaying step S14 may be performed.

When the avalanche amplification occurs, a notable change in the electrical property value occurs at the electric field concentration position. Thus, this change is observed, for example, as a change in contrast in the electrical property image. Accordingly, in step S15, it can be accurately determined based on the electrical property image whether or not the avalanche amplification occurs.

In the voltage applying step S11, an operator may, for example, input an arbitrary reverse bias voltage value at each step, or may, for example, increase a reverse bias voltage value by pushing a voltage rise button by the operator displayed on the monitor device 30. Further, the control system 28 may calculate an increase amount of the reverse bias voltage at each step based on the maximum allowable voltage value, and the control system 28 may automatically increase the reverse bias voltage by inputting instructions from the operator.

Further, in the displaying step S14, the monitor device 30 preferably simultaneously displays the plurality of electrical property images, respectively corresponding to the plurality of reverse bias voltage values that are sequentially applied in the voltage applying step S11, so that it is easy to check whether or not the avalanche amplification occurs. Further, the control system 28 may function also as a determination unit that determines whether or not the avalanche amplification occurs based on the plurality of electrical property images respectively corresponding to the plurality of reverse bias voltage values that are sequentially applied to the semiconductor device 32.

To be specific, for example, when the control system 28 calculates a difference between the plurality of electrical property images, and a contrast difference is greater than a predetermined threshold value, it can be determined in the determining step S15 that the avalanche amplification occurs. In this case, the difference may be taken with the electrical property image at an applied voltage (e.g., 0 V) at which no avalanche amplification occurs definitely, but the difference is preferably taken with the electrical property image acquired prior to raising the applied voltage. Otherwise, when a portion at which the contrast difference is greater than the predetermined threshold value has a greater area than a predetermined area, it may be determined that the avalanche amplification occurs. As it is determined in this way whether or not the avalanche amplification is present, incorrect determination caused by, for example, noise can be effectively prevented.

In addition, in the determining step S15, the determination unit may determine whether or not the avalanche amplification occurs from one electrical property image at a certain applied voltage. For example, in the determining step S15, when the determination unit finds an area of a region on which a contrast value in one electrical property image at a certain applied voltage is equal to or greater than a predetermined threshold value and the found area is greater than a predetermined area, it may be determined that the avalanche amplification occurs.

Afterward, when it is determined from the electrical property images displayed on the monitor device 30 that the avalanche amplification occurs in the semiconductor device 32 (Yes in step S15 in FIG. 3), a position at which electrical property value is locally great, i.e., the electric field concentration position, is identified based on the electrical property image that is finally acquired (step S16 in FIG. 3).

When there are a plurality of positions at which the electrical property value is locally great, there is a need to identify a position at which the electric field is more easily concentrated. Therefore, the applied voltage is increased by an increase value lower than an increase value of the voltage in the voltage applying step S11 so far, and the electrical property image is acquired. Thus, this electrical property image is compared with the electrical property images acquired so far, and a position at which a change of the electrical property value over the increase value of the voltage is great is identified as the electric field concentration position. Thereby, it is possible to identify the position at which the electric field is more easily concentrated. Here, positions may be ranked as the position at which the electric field is easily concentrated in order from the position at which the change of the electrical property value over the increase value of the voltage is great.

Figure 4:
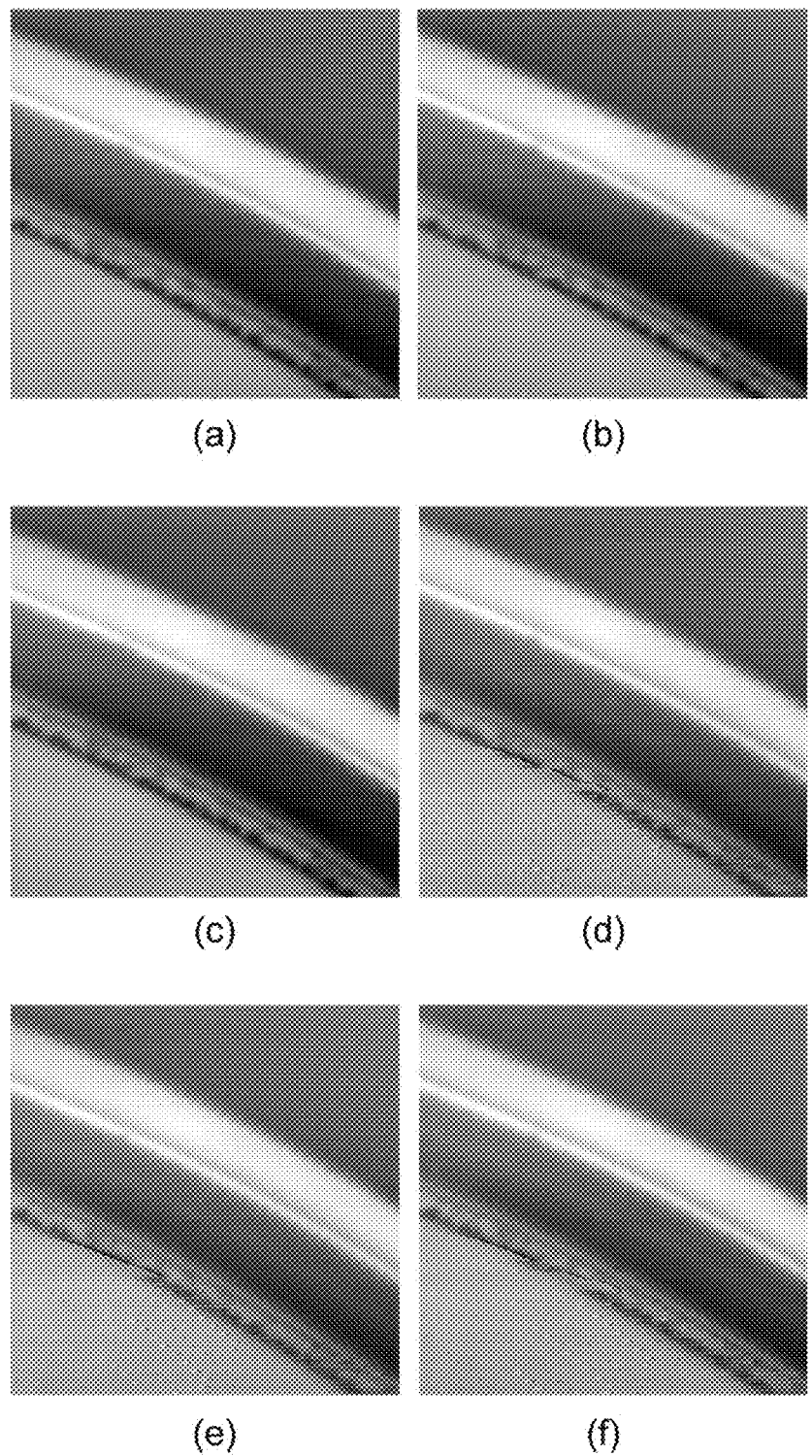
FIG. 4 includes (a)-(f) views showing examples of electrical property images.
Figure 5:
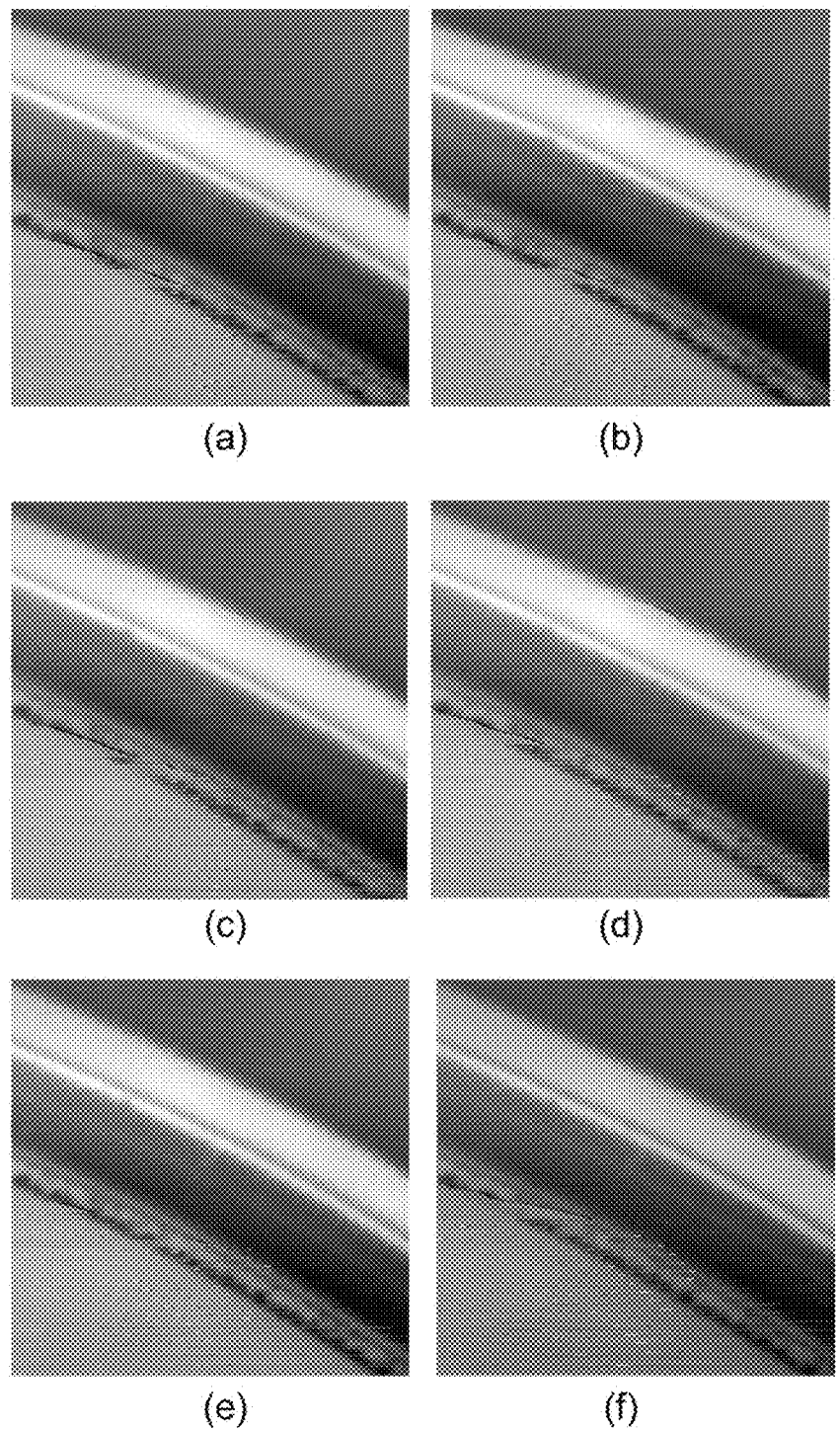
FIG. 5 includes (a)-(f) views showing examples of electrical property images.
Figure 6:
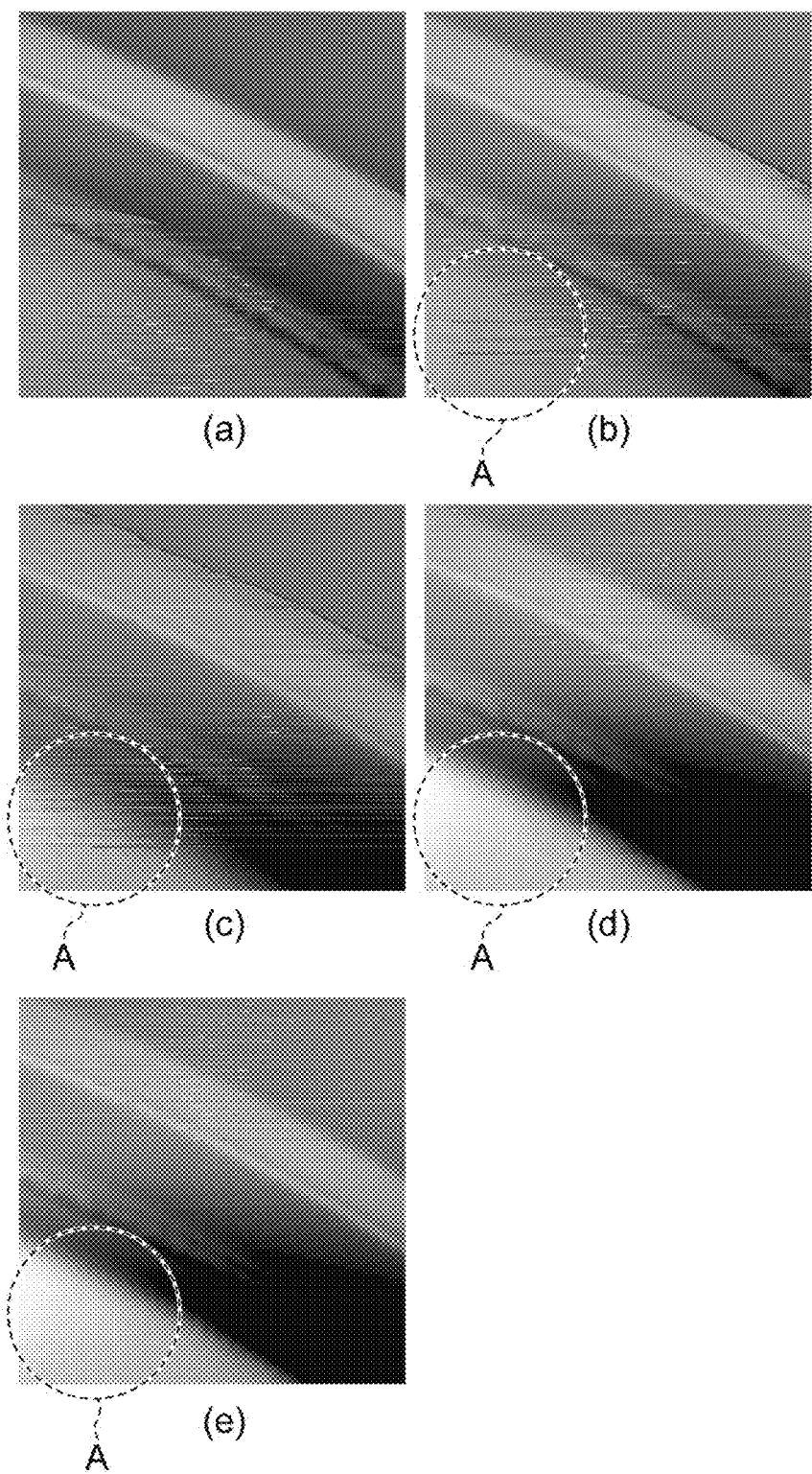
FIG. 6 includes (a) (e) views showing examples of electrical property images.

Here, FIG. 4 to FIG. 6 include views illustrating examples of the electrical property images as one example. (a) in FIG. 4 to (f) in FIG. 4 illustrate the electrical property images when the reverse bias voltages are set to 0 V, 5 V, 10 V, 15 V, 20 V, and 25 V, respectively. (a) in FIG. 5 to (f) in FIG. 5 illustrate the electrical property images when the reverse bias voltages are set to 30 V, 35 V, 40 V, 45 V, 50 V, and 55 V, respectively. (a) in FIG. 6 to (e) in FIG. 6 illustrate the electrical property images when the reverse bias voltages are set to 60 V, 65 V, 70 V, 75 V, and 80 V, respectively.

Referring to FIG. 4 to FIG. 6, when the reverse bias voltage is set to 65 V to 80 V ((b) in FIG. 6 to (e) in FIG. 6), lower left portions A of images become bright compared to previous images (FIG. 4, FIG. 5, and (a) in FIG. 6), and it is found that the avalanche amplification occurs at such portions. In this example, since the observation is performed using the semiconductor device 32 having a maximum allowable voltage value of 80 V, no avalanche breakdown phenomenon occurs even at a maximum reverse bias voltage (80 V).

Here, examples of application of the observation apparatus 10A and the observation method according to the present embodiment may include identifying a failure part in the sample of the semiconductor device 32 in which withstand voltage performance is lower than a prescribed value and a leak current is great. To be specific, for a sample in which an excessive current flows compared to a non-defective product when the reverse bias voltage is gradually increased, while the reverse bias voltage is gradually increased from the reverse bias voltage value at which the OBIC begins to increase to the vicinity of the maximum allowable voltage value before the avalanche breakdown phenomenon occurs, the electrical property images may be acquired whenever the reverse bias voltage is increased. The plurality of electrical property images obtained in this way are compared with each other, and the electrical property image in which the electrical property caused by the OBIC is sharply changed is identified, and thereby, the failure part can be identified.

Effects obtained by the observation apparatus 10A and the observation method of the present embodiment described above will be described.

According to the observation apparatus 10A and the observation method of the present embodiment, the electric field concentration part is observed by visualizing the electrical properties that occur in the semiconductor device 32 due to the laser light and are based on the OBIC. Accordingly, the electric field concentration position can be identified with a high resolution. Further, since the magnitude of the reverse bias voltage applied to the semiconductor device 32 is maintained to such an extent that the avalanche amplification occurs before the avalanche breakdown phenomenon occurs, it is possible to suppress damage to the semiconductor device 32. Thus, according to the observation apparatus 10A and the observation method of the present embodiment, while reducing a probability of the semiconductor device 32 being damaged, the semiconductor device 32 can be adequately observed, and the electric field concentration part can be accurately found. Further, the semiconductor device 32 is observed without being damaged by, for example, an electron microscope, and thereby the reason for which the electric field is concentrated can be analyzed.

In addition, according to the observation apparatus 10A and the observation method of the present embodiment, after the electrical property images are acquired while the reverse bias voltage is gradually raised from a sufficiently low voltage value, and a great change of the electrical property according to the avalanche amplification is detected, the increase of the reverse bias voltage can be stopped. Accordingly, even when the maximum allowable voltage value of the semiconductor device 32 is unclear, the damage to the semiconductor device 32 can be avoided.

(Second Embodiment)

Figure 7:
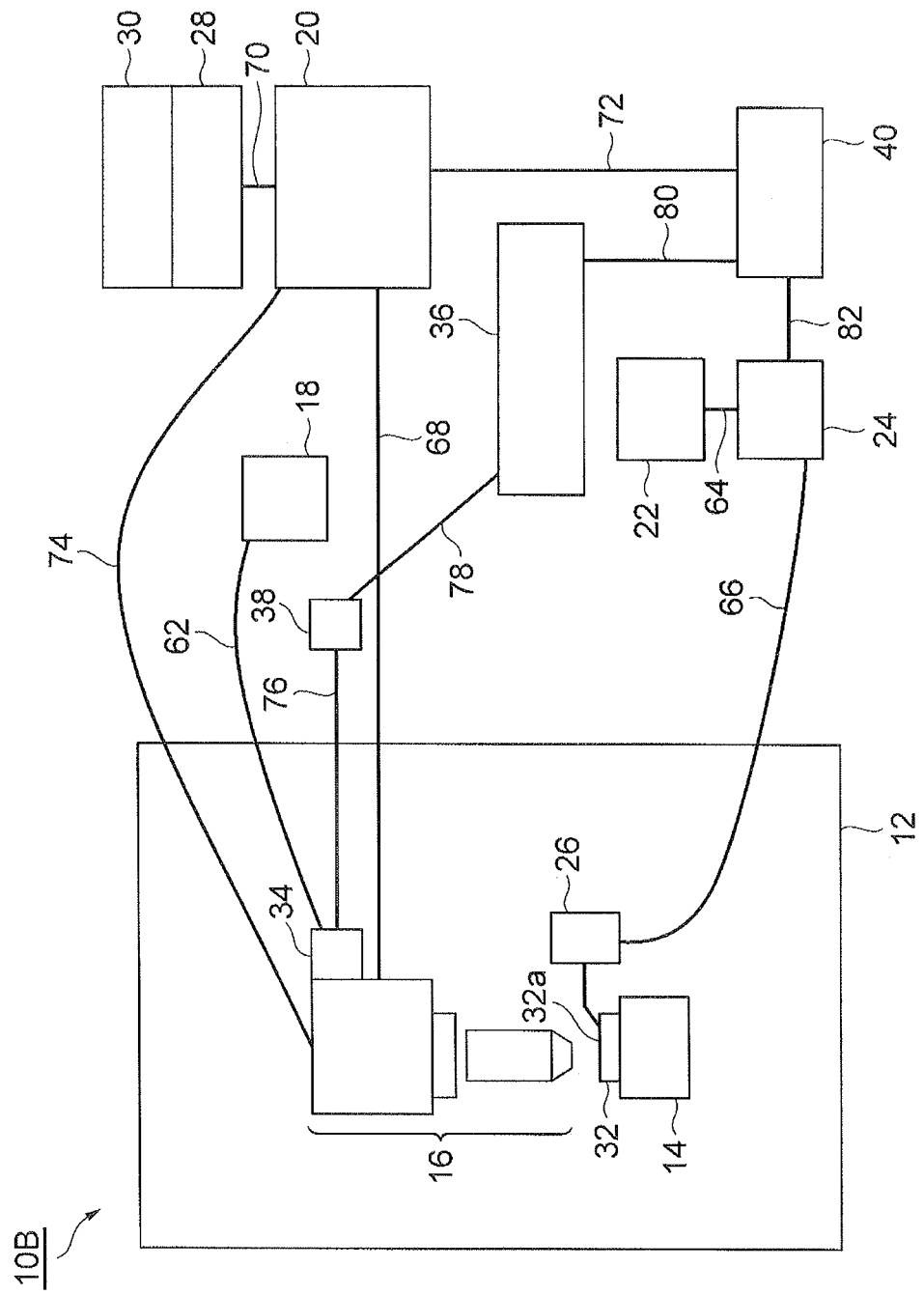
FIG. 7 is a block diagram schematically illustrating a configuration of an electric field concentration position observation apparatus according to a second embodiment.

Next, an electric field concentration position observation apparatus and an electric field concentration position observation method according to a second embodiment of the present invention will be described. FIG. 7 is a block diagram schematically illustrating a configuration of an observation apparatus 10B of the present embodiment. Points in which the observation apparatus 10B and the observation method of the present embodiment are different from the observation apparatus 10A and the observation method of the first embodiment are as follows.

In the observation apparatus 10B of the present embodiment, a laser light source 18 outputs laser light having a suitable wavelength in order to generate multiphoton absorption such as two-photon absorption or three-photon absorption in a semiconductor device 32. To be specific, in the case of the two-photon absorption, preferably, photon energy of the laser light is smaller than band gap energy of an observation object portion, and is greater than ½ of the band gap energy. Further, when the multiphoton absorption greater than three-photon absorption is to be sufficiently generated, the photon energy of the laser light may be about ⅓ of the band gap energy of the observation object portion. Accordingly, when the observation object portion is formed of Si, the wavelength of the laser light is preferably 1.2 μm or more, and more preferably 1.6 μm or less.

Further, the laser light source 18 is preferably a so-called femtosecond laser light source that outputs pulsed laser light whose pulse width is shorter than 1 picosecond. This is because the multiphoton absorption is easily generated in the semiconductor device 32 by irradiating with laser light having high power within a short time. When the laser light source 18 has an intensity of the laser light by which the multiphoton absorption is generated in the semiconductor device 32, a CW (Continuous Wave) laser light source that continuously outputs laser light may be used as the laser light source 18.

Further, the observation apparatus 10B of the present embodiment further includes an AO module 34, a pulse generator 36, an AO module amplifier 38, and a lock-in amplifier 40. The AO module 34 modulates the pulsed laser light output from the laser light source 18 in a lower frequency in the irradiating and detecting step S12 illustrated in FIG. 3, and provides the modulated laser light to the scanning optical system 16. The AO module 34 is electrically coupled to the AO module amplifier 38 via a control cable 76, and the AO module amplifier 38 is electrically coupled to the pulse generator 36 via a control cable 78. The pulse generator 36 gives a control signal for controlling the AO module amplifier 38 to the AO module amplifier 38 through the control cable 78. The AO module amplifier 38 generates a modulation signal for modulating the laser light based on this control signal, and outputs the signal to the AO module 34.

The lock-in amplifier 40 is electrically coupled to the pulse generator 36 via a cable 80, and is also electrically coupled to a sensor 24 via a cable 82. The lock-in amplifier 40 receives the control signal for controlling the AO module amplifier 38 from the pulse generator 36 in the irradiating and detecting step S12 illustrated in FIG. 3, sets a detection frequency based on the control signal, and extracts a signal component corresponding to the detection frequency from an output signal from the sensor 24 (lock-in detection). The signal component extracted in this way is sent to a control system 28 via cables 72 and 70. The control system 28 performs mapping based on the signal component and information on a scanning position in the image generating step S13 illustrated in FIG. 3, and thereby generates an electrical property image of the semiconductor device 32.

The observation apparatus 10B of the present embodiment includes the AO module 34, the pulse generator 36, the AO module amplifier 38, and the lock-in amplifier 40, however, it goes without saying that these are not required when the CW laser light source is used as the laser light source. In this case, a configuration and operation of the sensor 24 are as described in the first embodiment. In the first embodiment, when the pulsed laser light source is used as the laser light source, the AO module 34, the pulse generator 36, the AO module amplifier 38, and the lock-in amplifier 40 may be provided as in the observation apparatus 10B of the present embodiment. In that case, configurations and operations are as described above.

According to the observation apparatus 10B and the observation method of the present embodiment described above, similar to the first embodiment, the semiconductor device 32 can be adequately observed while reducing a probability of damage to the semiconductor device 32, and the electric field concentration position can be accurately found with a high resolution. Here, in the present embodiment, the lock-in detection is performed at the lock-in amplifier 40, and thereby an S/N ratio is improved, however, the configuration for performing the lock-in detection may be omitted.

In addition, the determination unit (determining step) for determining whether or not the avalanche amplification occurs may compare the plurality of electrical property images having different applied voltages with one another. In this case, it can be relatively determined whether or not the avalanche amplification is present. To be specific, the comparison with the electrical property image acquired prior to raising the applied voltage is preferably performed. If the voltage is applied, a contrast value may be increased on the whole by the influence of, for example, noise. Thus, the comparison of the electrical property image with the electrical property image acquired prior to raising the applied voltage is performed, and thereby it is possible to be safe from the influence of noise. Further, when a difference between the plurality of electrical property images having different applied voltages is calculated and a contrast difference is greater than a predetermined threshold value, the determination unit may determine that the avalanche amplification occurs. In this case, it is possible to reliably determine whether or not the avalanche amplification is present.

Further, when a portion at which a contrast difference between the plurality of electrical property images having different applied voltages is greater than a predetermined threshold value has a greater area than a predetermined area, the determination unit (determining step) may determine that the avalanche amplification occurs. As it is determined in this way whether or not the avalanche amplification is present, incorrect determination caused by, for example, noise can be effectively prevented.

In addition, similar to the first embodiment, when there are a plurality of positions at which the electrical property value is locally great, the applied voltage may be increased by an increase value lower than an increase value of the voltage in the voltage applying step S11 so far, the electrical property image may be acquired, this electrical property image may be compared with the electrical property images acquired so far, and a position at which a change of the electrical property value over the increase value of the voltage is great may be identified as the electric field concentration position. Thereby, it is possible to identify the position at which the electric field is more easily concentrated. Further, positions may be ranked as the position at which the electric field is easily concentrated in order from the position at which the change of the electrical property value over the increase value of the voltage is great.

The electric field concentration position observation apparatus and the electric field concentration position observation method according to the present invention are not limited to the above-described embodiments, and various other modifications are possible. For example, in each of the above-described embodiments, the power transistor is taken as the example of the semiconductor device, but the semiconductor device that can be observed by the present invention is not limited thereto, and for example, various other semiconductor devices capable of generating the avalanche amplification such as a power device or an avalanche photodiode may be observed.

The electric field concentration position observation apparatus according to the above-described embodiment is an apparatus for observing an electric field concentration position in a semiconductor device, and includes a laser light source, an irradiation optical system that irradiates the semiconductor device with laser light output from the laser light source, a voltage application unit that applies a predetermined voltage between electrodes of the semiconductor device, a detection unit that detects an electrical property occurring in the semiconductor device due to the laser light, and an image generation unit that generates an electrical property image of the semiconductor device based on a detection signal from the detection unit, and in the apparatus, the voltage application unit gradually increases a magnitude of the predetermined voltage until the predetermined voltage reaches a voltage at which avalanche amplification occurs in the semiconductor device, and when the predetermined voltage is increased, the irradiation optical system irradiates with the laser light, the detection unit detects the electrical property, and the image generation unit generates the electrical property image.

Further, the electric field concentration position observation method according to the above-described embodiment is a method for observing an electric field concentration position in a semiconductor device, and includes a voltage applying step of applying a predetermined voltage between electrodes of the semiconductor device, an irradiating and detecting step of irradiating the semiconductor device with laser light and detecting an electrical property occurring in the semiconductor device due to the laser light, and an image generating step of generating an electrical property image of the semiconductor device based on a detection signal obtained in the irradiating and detecting step, and in the method, while the predetermined voltage is gradually increased in the voltage applying step until the predetermined voltage reaches a voltage at which avalanche amplification occurs in the semiconductor device, the voltage applying step, the irradiating and detecting step, and the image generating step are repeatedly performed.

Further, the electric field concentration position observation apparatus may be configured such that the laser light source outputs pulsed laser light having a pulse width shorter than 1 picosecond and a wavelength of 1200 nm or more. Similarly, the electric field concentration position observation method may be configured such that, in the irradiating and detecting step, the semiconductor device is irradiated with pulsed laser light having a pulse width shorter than 1 picosecond and a wavelength of 1200 nm or more.

Further, the electric field concentration position observation apparatus may be configured to further include a determination unit that determines whether or not the avalanche amplification occurs based on the plurality of electrical property images respectively corresponding to the plurality of predetermined voltages sequentially applied from the voltage application unit. Similarly, the electric field concentration position observation method may be configured to further include a determining step of determining whether or not the avalanche amplification occurs based on the plurality of electrical property images respectively corresponding to the plurality of predetermined voltages sequentially applied in the voltage applying step.

In addition, the electric field concentration position observation apparatus may be configured to further include a determination unit that determines whether or not the avalanche amplification occurs based on the electrical property image corresponding to the predetermined voltage applied from the voltage application unit. Similarly, the electric field concentration position observation method may be configured to further include a determining step of determining whether or not the avalanche amplification occurs based on the electrical property image corresponding to the predetermined voltage applied in the voltage applying step.

Further, the electric field concentration position observation apparatus may be configured to further include a display unit that simultaneously displays the plurality of electrical property images respectively corresponding to the plurality of predetermined voltages sequentially applied from the voltage application unit. Similarly, the electric field concentration position observation method may be configured to further include a displaying step of simultaneously displaying the plurality of electrical property images respectively corresponding to the plurality of predetermined voltages sequentially applied in the voltage applying step.

Further, the electric field concentration position observation apparatus may be configured such that the voltage application unit uses a value obtained by subtracting a predetermined value from a maximum allowable voltage value specified for the semiconductor device as a magnitude of a first predetermined voltage. Similarly, the electric field concentration position observation method may be configured such that, in the voltage applying step, a value obtained by subtracting a predetermined value from a maximum allowable voltage value specified for the semiconductor device is used as a magnitude of a first predetermined voltage.

INDUSTRIAL APPLICABILITY

The present invention can be used for an electric field concentration position observation apparatus and an electric field concentration position observation method through which an electric field concentration position can be accurately found.

REFERENCE SIGNS LIST 10A, 10B—observation apparatus, 12—dark box, 14—stage, 16—scanning optical system, 18—laser light source, 20—laser scan controller, 22—bias power supply, 24—sensor, 26—probing system, 28—control system, 30—monitor device, 32—semiconductor device, 32a—laser irradiation surface, 34—AO module, 36—pulse generator, 38—AO module amplifier, 40—lock-in amplifier, La—laser light.

The invention claimed is:

1. An apparatus for observing an electric field concentration position in a semiconductor device, the apparatus comprising:
a laser light source;
an irradiation optical system configured to irradiate the semiconductor device with laser light output from the laser light source;
a voltage application unit configured to apply a predetermined voltage between electrodes of the semiconductor device;
a sensor configured to detect an electrical property occurring in the semiconductor device in response to irradiation of the laser light and output a detection signal; and
an image generation unit electrically coupled to the sensor and configured to generate one of a plurality of electrical property images of the semiconductor device based on the detection signal, wherein
the voltage application unit gradually increases a magnitude of the predetermined voltage until the predetermined voltage reaches a voltage at which avalanche amplification occurs in the semiconductor device; and
the apparatus further comprises a determination unit electrically coupled to the sensor and configured to determine whether the avalanche amplification occurs based on the one of the plurality electrical property images corresponding to the predetermined voltage applied form the voltage application unit.

2. The apparatus according to claim 1, wherein the laser light source outputs pulsed laser light having a pulse width shorter than 1 picosecond and a wavelength of 1200 nm or more.

3. The apparatus according to claim 1, wherein
the voltage application unit sequentially applies, as the predetermined voltage, a plurality of predetermined voltages between electrodes,
the image generation unit generates, as the one of the plurality of electrical property images, the plurality of electrical property images respectively corresponding to the plurality of predetermined voltages, and
the determination unit determines whether the avalanche amplification occurs based on the plurality of electrical property images.

4. The apparatus according to claim 1, wherein
the voltage application unit sequentially applies, as the predetermined voltage, a plurality of predetermined voltages between the electrodes,
the image generation unit generates, as the one of the plurality of electrical property images, the plurality of electrical property images respectively corresponding to the plurality of predetermined voltages, and
the apparatus further comprises a display configured to simultaneously display the plurality of electrical property images.

5. The apparatus according to claim 1, wherein the voltage application unit uses a value obtained by subtracting a predetermined value from a maximum allowable voltage value specified for the semiconductor device as a magnitude of a first predetermined voltage.

6. The apparatus according to claim 1, wherein, when the predetermined voltage is increased, the irradiation optical system irradiates with the laser light, the sensor detects the electrical property, and the image generation unit generates the electrical property image.

7. A method for observing an electric field concentration position in a semiconductor device, the method comprising:
applying a predetermined voltage between electrodes of the semiconductor device;
irradiating the semiconductor device with laser light;
detecting an electrical property occurring in the semiconductor device in response to irradiation of the laser light and outputting a detection signal; and
generating one of a plurality of electrical property images of the semiconductor device based on the detection signal, wherein
the applying, the irradiating, the detecting, and the generating are repetitively performed while the predetermined voltage is gradually increased in the applying until the predetermined voltage reaches a voltage at which avalanche amplification occurs in the semiconductor device, and
the method further comprises determining whether the avalanche amplification occurs based on the one of the plurality of electrical property images corresponding to the predetermined voltage in the applying.

8. The method according to claim 7, wherein, in the irradiating, the semiconductor device is irradiated with pulsed laser light having a pulse width shorter than 1 picosecond and a wavelength of 1200 nm or more.

9. The method according to claim 7, wherein
in the applying, as the predetermined voltage, a plurality of predetermined voltages are sequentially applied between the electrodes,
in the generating, as the one of the plurality of electrical property images, the plurality of electrical property images respectively corresponding to the plurality of predetermined voltages are generated, and
in the determining, whether the avalanche amplification occurs is determined based on the plurality of electrical property images.

10. The method according to claim 7, wherein
in the applying, as the predetermined voltage, a plurality of predetermined voltages are sequentially applied between the electrodes,
in the generating, as the one of the plurality of electrical property images, the plurality of electrical property images respectively corresponding to the plurality of predetermined voltages are generated, and
the method further comprises simultaneously displaying the plurality of electrical property images.

11. The method according to claim 7, wherein, in the applying, a value obtained by subtracting a predetermined value from a maximum allowable voltage value specified for the semiconductor device is used as a magnitude of a first predetermined voltage.

\* \* \* \* \*